(12) United States Patent
Sibinga et al.

(10) Patent No.: US 10,441,687 B2
(45) Date of Patent: Oct. 15, 2019

(54) WNT/BETA-CATENIN INHIBITOR-ELUTING ENDOVASCULAR STENT

(71) Applicant: ALBERT EINSTEIN COLLEGE OF MEDICINE, INC., Bronx, NY (US)

(72) Inventors: Nicholas Ernst Smit Sibinga, Chappaqua, NY (US); Dario Fernando Riascos-Bernal, Bronx, NY (US)

(73) Assignee: Albert Einstein College of Medicine, Bronx, NY (US)

(*) Notice: Subject to any disclaimer, the term of this patent is extended or adjusted under 35 U.S.C. 154(b) by 271 days.

(21) Appl. No.: 15/028,449

(22) PCT Filed: Nov. 5, 2014

(86) PCT No.: PCT/US2014/064046
§ 371 (c)(1),
(2) Date: Apr. 11, 2016

(87) PCT Pub. No.: WO2015/073274
PCT Pub. Date: May 21, 2015

(65) Prior Publication Data
US 2016/0263289 A1    Sep. 15, 2016

Related U.S. Application Data

(60) Provisional application No. 61/903,666, filed on Nov. 13, 2013.

(51) Int. Cl.
*A61L 31/10* (2006.01)
*A61L 31/16* (2006.01)

(52) U.S. Cl.
CPC ............ *A61L 31/10* (2013.01); *A61L 31/16* (2013.01); *A61L 2300/432* (2013.01); *A61L 2420/06* (2013.01)

(58) Field of Classification Search
None
See application file for complete search history.

(56) References Cited

U.S. PATENT DOCUMENTS

| 2009/0117169 A1 | 5/2009 | Sibinga et al. |
| 2013/0261723 A1* | 10/2013 | Stankus ............ A61M 25/104 623/1.11 |
| 2014/0377285 A1* | 12/2014 | Liu ................. A61K 45/06 424/174.1 |

FOREIGN PATENT DOCUMENTS

| WO | WO-2009005269 A2 * | 1/2009 | ........ C07D 413/12 |
| WO | 2012135176 A2 | 10/2012 | |
| WO | 2013070976 A1 | 5/2013 | |

OTHER PUBLICATIONS

PCT International Search Report and Written Opinion, dated Feb. 18, 2015 in connection with PCT International Application No. PCT/US2014/064046, 8 pages.

* cited by examiner

*Primary Examiner* — David J Blanchard
*Assistant Examiner* — Daniel F. Coughlin
(74) *Attorney, Agent, or Firm* — Amster, Rothstein & Ebenstein LLP

(57) ABSTRACT

A product comprising a stent for a human blood vessel which comprises (i) a scaffold which is impregnated with, adsorbed with, or coated with an inhibitor of a Wnt/p-catenin pathway, or (ii) a scaffold coated with a polymer, which polymer is impregnated with, adsorbed with, or coated with an inhibitor of a Wnt/p-catenin pathway, and methods of use to reduce the risk of restenosis.

19 Claims, 11 Drawing Sheets

WNT/BETA-CATENIN INHIBITOR-ELUTING ENDOVASCULAR STENT

CROSS-REFERENEC TO RELATED APPLICATIONS

This application is a U.S. national stage entry under 35 U.S.C. § 371 of PCT International Patent. Application No. PCT/US2014/0646046, filed Nov. 5,2014, which claims benefit of U.S. Provisional Application No. 61/903,666, filed Nov. 13,2013, the contents of each of which are incorporated herein by reference into the subject application.

STATEMENT OF GOVERNMENT SUPPORT

This invention was made with government support under grant numbers R01HL088104 and R01HL104518 awarded by the National Institutes of Health. The government has certain rights in the invention.

BACKGROUND OF THE INVENTION

The disclosures of all publications, patents, patent application publications and books referred to in this application are hereby incorporated by reference in their entirety into the subject application to more fully describe the art to which the subject invention pertains.

In a significant number of patients suffering from atherosclerotic coronary artery disease, introduction of a catheter into the affected vessel, inflation of a balloon to relieve the obstruction (angioplasty), and implantation of a stent to maintain lumen permeability are performed as part of their treatment. Stents are small metal tubes or scaffolds that can be inserted via a balloon catheter into the narrowed segment of the artery. When the balloon is inflated, the stent expands and is embedded into the artery vessel wall, which thus opens the previously narrowed segment of artery. The balloon is then deflated and removed along with the catheter, and the stent is left behind to serve as a metal framework for the artery (FIG. 2). Although stented arteries have less chance of renarrowing (restenosis) than arteries opened with a balloon alone, in-stent restenosis can still occur in more than 1 in 5 patients after stent placement (FIG. 3). Because restenosis within the stented region of a heart artery is caused by tissue growth—mainly driven by proliferation, migration and matrix synthesis of vascular SMCs—some stents, called drug-eluting stents (DESs), are coated with medication that can be slowly released into the arterial wall to inhibit or prevent this tissue growth. DESs markedly reduce the rate of restenosis and the need of revascularization. In fact, about 1 in 10 patients develops restenosis in the first several years after drug-eluting stent implantation, a rate about half of that seen for stents without medication. However, current DESs have significant limitations. These DESs are designed to release pharmacological agents into the vessel wall in order to inhibit the response to injury causing restenosis; unfortunately, the action of agents currently in use is not confined to inhibition of SMCs, but extends to other cell types, including ECs. All the medications released by existing DESs decrease EC migration and proliferation; moreover, they induce EC expression of tissue factor, an important pro-coagulant glycoprotein. Existing DESs also decrease proliferation, differentiation, and homing of endothelial progenitor cells, which are believed to contribute to re-endothelialization after stent implantation. These inhibitory effects on EC biology result in delayed endothelialization (EC coverage) of stent struts, which leaves exposed stent components that trigger thrombosis and inflammation and may result in in-stent thrombosis and consequent myocardial infarction and death. In order to reduce the risk of in-stent thrombosis, patients treated with existing DES must receive a long-term dual antiplatelet therapy, usually a combination of aspirin and clopidogrel for at least 1 year, which increases the risk of bleeding and health care costs. Existing DES cannot be used in patients in whom this prolonged antiplatelet therapy is contraindicated.

The present invention addresses the need for improved stents which encourage endothelialization and inhibit restenosis.

SUMMARY OF THE INVENTION

This invention provides a product comprising a stent for a human blood vessel which comprises (i) a scaffold coated with a polymer, which polymer is impregnated with, adsorbed with, or coated with an inhibitor of a Wnt/β-catenin pathway, or (ii) a scaffold which is impregnated with, adsorbed with, or coated with, an inhibitor of a Wnt/β-catenin pathway.

This invention also provides a method for performing an angioplasty in a mammalian subject comprising surgically inserting a stent of the invention as described herein into the a vascular vessel and expanding the stent so as perform the angioplasty.

This invention also provides a method for improving a vascular vessel luminal diameter in a mammalian subject comprising surgically inserting a stent of the invention as described herein into the lumen of the vascular vessel and expanding the stent so as to improve vascular vessel luminal diameter.

This invention also provides a method for reducing restenosis in a vascular vessel at risk for restenosis of a mammalian subject comprising surgically inserting a stent of the invention as described herein into the lumen of the vascular vessel at the site deemed at risk of restenosis, so as to reduce the risk of restenosis.

This invention also provides a method of reducing the risk of a thrombotic event in a vascular vessel following angioplasty of the vascular vessel comprising surgically inserting a stent of the invention as described herein into the lumen of the vascular vessel in need of angioplasty, expanding the stent to effect the angioplasty and increase the lumen of the vascular vessel under conditions permitting the inhibitor of a Wnt/β-catenin pathway to elute from the stent thereby reducing the risk of a thrombotic event in a vascular vessel following angioplasty.

This invention also provides method for treating a restenosis in a vascular vessel of a mammalian subject having restenosis in a vascular vessel comprising surgically inserting a stent of the invention as described herein into the vascular vessel at the site of restenosis.

DETAILED DESCRIPTION OF THE INVENTION

Figures 1A, 1B, 1C:
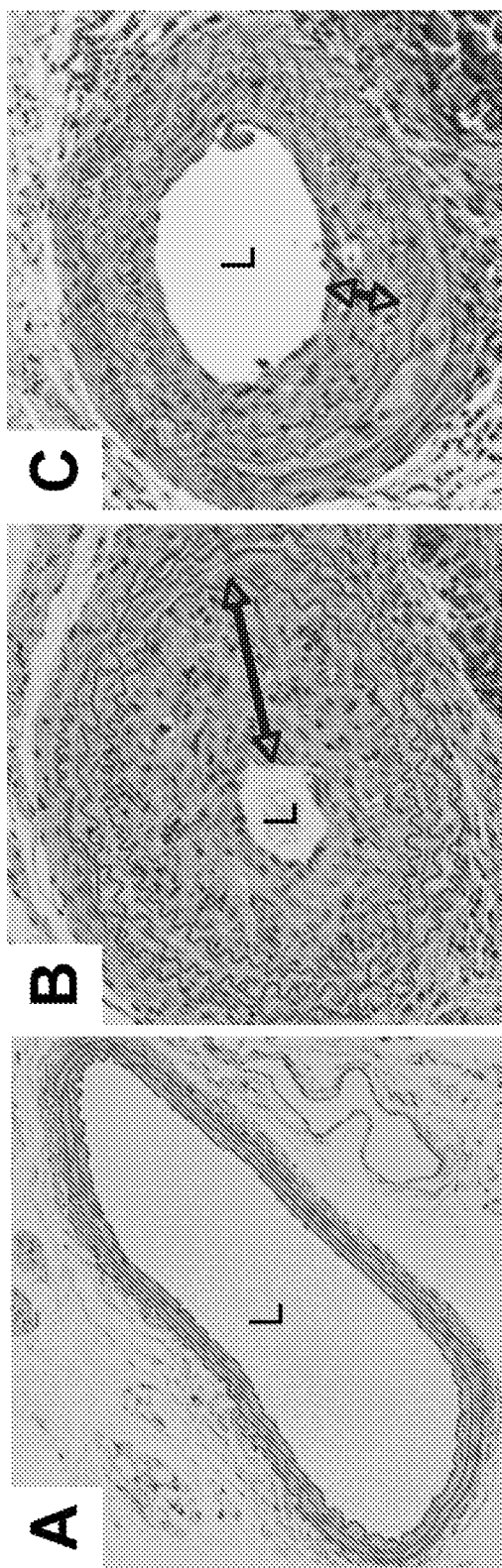
FIG. 1A-1C: Beta-catenin inactivation in Vascular Smooth Muscle Cells Decreases Stenosis After Vascular Injury. A) Normal carotid artery. B) Carotid artery 21 days after ligation. Tissue growth, known as neointima (blue arrow), has narrowed the lumen (L) of the vessel (stenosis). C) Genetic inactivation of beta-catenin in vascular smooth muscle cells significantly reduces neointima formation (stenosis) after carotid artery ligation.
Figure 2:
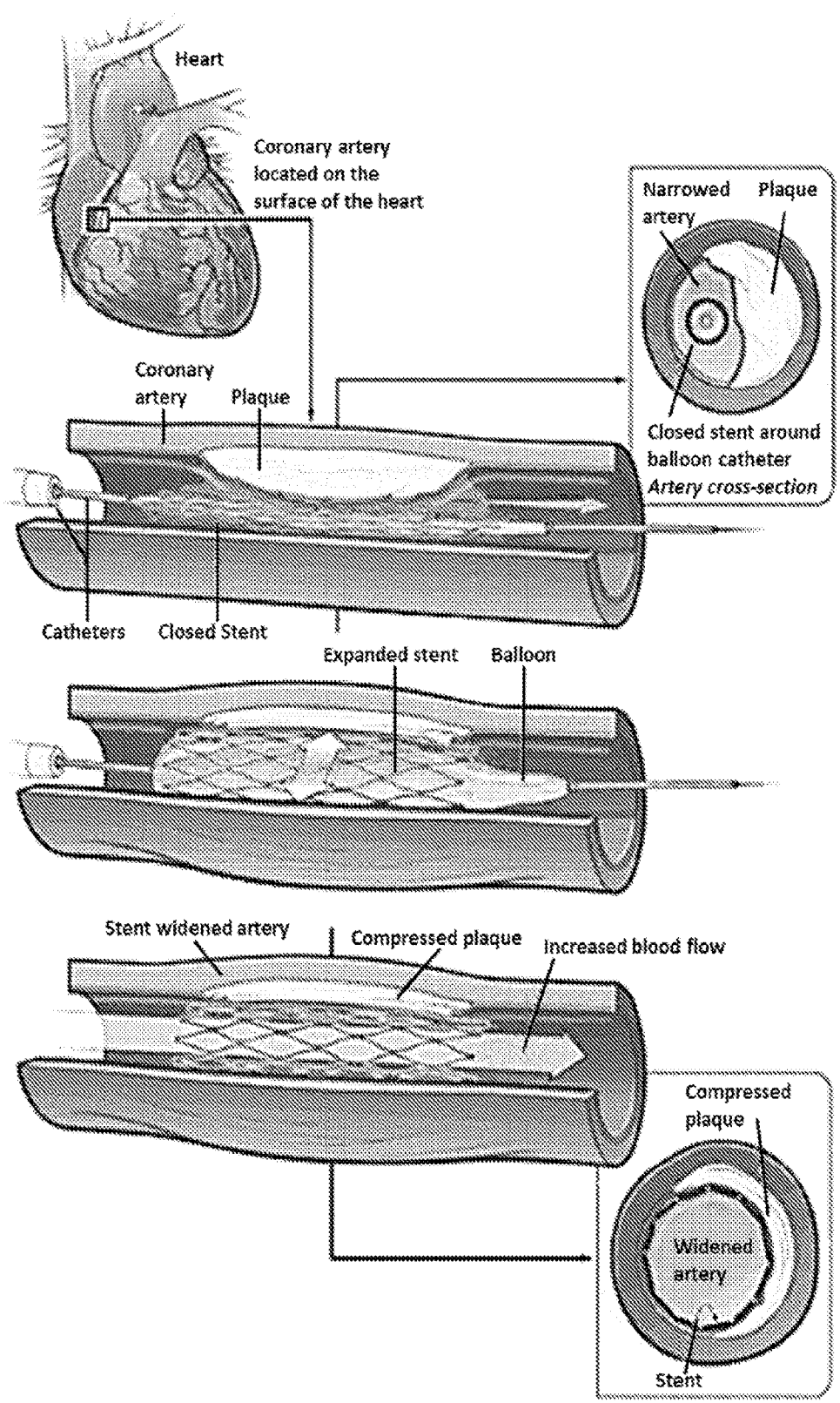
FIG. 2: Angioplasty and Stent Placement from Wikipedia as wiki/Coronary_stent as sourced from the world wide web as nhlbi.nih.gov/health/dci/Diseases/Angioplasty/Angioplasty_WhatIs.html.
Figures 3A, 3B, 3C:
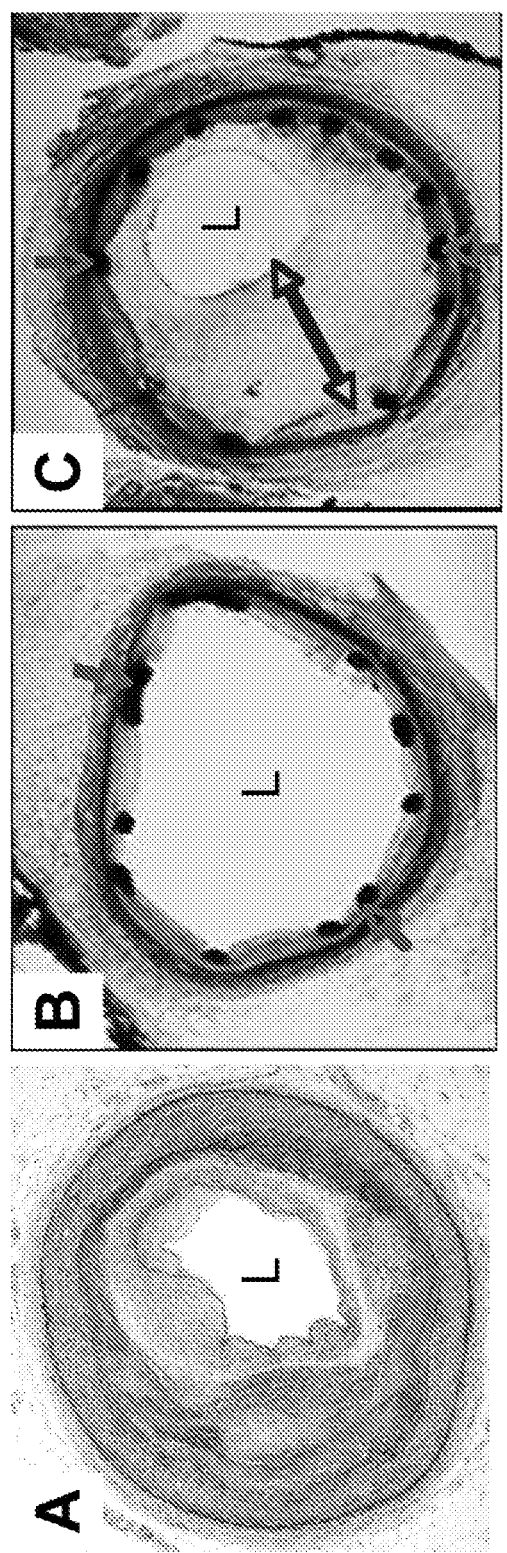
FIG. 3A-3C: In-stent Restenosis—A) Coronary artery with a large atherosclerotic plaque that narrows the lumen (L). B) Coronary artery after angioplasty and stent placement. The lumen of the artery has been restored. The green arrows indicate the stent struts. C) Restenosis after stent placement. Tissue growth, known as neointima (blue arrow), has renarrowed the lumen of the vessel. Green arrows show the stent struts Modified from en.Wikipedia as wiki/Atherosclerosis and www.hkma.org/english/cme/clinicalcase/200703 a_set.htm.

This invention provides a product comprising a stent for a human blood vessel which comprises (i) a scaffold coated with a polymer, which polymer is impregnated with, adsorbed with, or coated with an inhibitor of a Wnt/β-catenin pathway, or (ii) a scaffold which is impregnated with, adsorbed with, or coated with, an inhibitor of a Wnt/β-catenin pathway.

In an embodiment, the stent is a shaped to be suitable as an endovascular stent.

In an embodiment, at least 50% the inhibitor of a Wnt/β-catenin pathway elutes from the stent.

In an embodiment, at least 90% of the inhibitor of a Wnt/β-catenin pathway elutes from the stent over a time period of 1 to 150 days. In an embodiment, the Wnt/β-catenin pathway elutes from the stent in a moist environment in contact with the stent. In an embodiment, the moist environment comprises a blood vessel.

In an embodiment, the stent comprises a scaffold impregnated with, adsorbed with, or coated with, an inhibitor of a Wnt/β-catenin pathway.

In an embodiment, the stent comprises a scaffold coated with a polymer impregnated with, adsorbed with, or coated with an inhibitor of a Wnt/β-catenin pathway.

In an embodiment, the inhibitor of a Wnt/β-catenin pathway is adsorbed within the polymer and/or adsorbed to a surface of the polymer.

In an embodiment, the inhibitor of a Wnt/β-catenin pathway is coated on the polymer.

In an embodiment, the polymer is not prothrombotic. In an embodiment, the polymer is a synthetic polymer. In an embodiment, it is a hydrocarbon-based polymer.

In an embodiment, the polymer comprises one or more of poly(n-butyl methacrylate), poly(ethylene-co-vinyl acetate), poly(styrene-b-isobutylene-b-styrene) or poly(vinylidene fluoride-co-hexafluoropropylene).

In an embodiment, the polymer comprises phosphorylcholine.

In an embodiment, the polymer is durable.

In an embodiment, the polymer is biodegradable.

In an embodiment, the stent is bioresorbable.

In an embodiment, the stent is balloon-expandable or self-expandable.

In an embodiment, the inhibitor of a Wntβ-catenin pathway is a small organic molecule.

In an embodiment, the inhibitor of a Wnt/β-catenin pathway is an antibody or an antigen-binding fragment of an antibody.

In an embodiment, the inhibitor targets a Wnt ligand, Frizzled protein (FZD), low density lipoprotein receptor-related protein 5 (LRP5) or LRP 6, Dishevelled protein (Dvl), axin, adenomatous polyposis *coli* (APC) tumor suppressor protein, glycogen synthase kinase 3β (GSK3β), casein kinase 1 (CK1), protein phosphatase 2A (PP2A), tankyrase 1, tankyrase 2, porcupine, (β-catenin, a member of the DNA-binding T cell factor/lymphoid enhancer factor (TCF/LEF) family protein, a (β-catenin C-terminal co-activator, or a (β-catenin N-terminal co-activator.

In an embodiment, the inhibitor of a Wnt/β-catenin pathway is an anti-Wnt 1 antibody or an antigen-binding fragment thereof, or an anti-Wnt 2 antibody or an antigen-binding fragment thereof, or an anti-FZD antibody or an antigen-binding fragment thereof In an embodiment, the scaffold of the stent comprises metal or a metal alloy.

In an embodiment, the scaffold of the stent comprises stainless steel, cobalt—chromium or platinum—chrome.

This invention also provides a method for performing an angioplasty in a mammalian subject comprising surgically inserting a stent of the invention as described herein into the a vascular vessel and expanding the stent so as perform the angioplasty.

This invention also provides a method for improving a vascular vessel luminal diameter in a mammalian subject comprising surgically inserting a stent of the invention as described herein into the lumen of the vascular vessel and expanding the stent so as to improve vascular vessel luminal diameter.

This invention also provides a method for reducing restenosis in a vascular vessel at risk for restenosis of a mammalian subject comprising surgically inserting a stent of the invention as described herein into the lumen of the vascular vessel at the site deemed at risk of restenosis, so as to reduce the risk of restenosis.

This invention also provides a method of reducing the risk of a thrombotic event in a vascular vessel following angioplasty of the vascular vessel comprising surgically inserting a stent of the invention as described herein into the lumen of the vascular vessel in need of angioplasty, expanding the stent to effect the angioplasty and increase the lumen of the vascular vessel under conditions permitting the inhibitor of a Wnt/β-catenin pathway to elute from the stent thereby reducing the risk of a thrombotic event in a vascular vessel following angioplasty.

This invention also provides method for treating a restenosis in a vascular vessel of a mammalian subject having restenosis in a vascular vessel comprising surgically inserting a stent of the invention as described herein into the vascular vessel at the site of restenosis.

In an embodiment, the vascular vessel is not a CNS vascular vessel.

In an embodiment, the vascular vessel is a coronary vascular vessel.

In an embodiment, the subject has symptomatic ischemic disease.

In an embodiment, the subject has an atherosclerotic disease of the vascular vessel.

In an embodiment, the subject has undergone an angioplasty of the vascular vessel.

In an embodiment, the inhibitor targets (directly or indirectly) a component of a Wnt/β-catenin pathway and results in decreased levels and/or activity of β-catenin in a cell. Molecular targets include but are not limited to: Wnt ligands, Frizzled protein (FZD), low density lipoprotein receptor-related protein 5 (LRP5) or LRP6, Dishevelled protein (Dvl), axin, adenomatous polyposis *coli* (APC) tumour suppressor protein, glycogen synthase kinase 3β (GSK3β), casein kinase 1 (CK1), protein phasphatase 2A (PP2A), tankyrase 1, tankyrase 2, porcupine, β-catenin, members of the DNA-binding T cell factor/lymphoid enhancer factor (TCF/LEF) family proteins (e.g., TCF1, TCF3, TCF4, Lefl), β-catenin C-terminal co-activators (e.g., CBP, p300, Tip60, MED12, parafibromin, TBP, Brg-1, ISW1, TRRAP, MLL1), β-catenin N-terminal co-activators (e.g., BCL9, BCL9L).

In an embodiment, the impregnated, adsorbed, or coated inhibitor of a Wnt/β-catenin pathway is all, or is substantially all, on the internal lumen of the stent.

As used herein, "treating" a condition means lessening or ameliorating one or more symptoms or one or more hallmarks of the condition.

As used herein a "small organic molecule" is a small molecule comprising carbon and of 2,000 Daltons or less. In an embodiment, the small organic molecule is of 1,500 Daltons or less. In an embodiment, the small organic molecule is of 1,000 Daltons or less.

In an embodiment, the stent comprises a metallic scaffold which is partially or completely covered by a polymer.

In one embodiment, the present invention includes a durable polymer coated stent that releases an inhibitor of the Wnt/beta-catenin signaling that interferes with Wnt/Receptor interactions. In one embodiment, this stent releases an inhibitor of Wnt/beta-catenin that modifies cytosolic events involved in the signaling process. In one embodiment, the present invention releases an inhibitor of Wnt/beta-catenin that interferes with nuclear interactions. In one embodiment, the present invention includes a metallic stent platform, and a durable polymer coating that releases an inhibitor of the Wnt/beta-catenin signaling. In one embodiment, this invention includes a metallic stent platform, a biodegradable polymer coating, and an inhibitor of the Wnt/beta-catenin signaling. In one embodiment, the present invention includes a fully bioresorbable vascular scaffold that releases an inhibitor of Wnt/beta-catenin signaling.

In an embodiment, the Wnt ligand, Wntl, Wnt2, Frizzled protein (FZD), Dvl, Tankyrase 1, Tankyrase 2, axin, porcupine, beat-catenin, CBP co-activator or TCF protein being inhibited is a human Wnt ligand, Wnt1, Wnt2, Frizzled protein (FZD), Dvl, Tankyrase 1, Tankyrase 2, axin, porcupine, beat-catenin, CBP co-activator or TCF protein.

In an embodiment wherein the inhibitor of a Wnt/β-catenin pathway is an antibody, or an antigen-binding fragment thereof, the antibody is a chimeric antibody. In an embodiment wherein the inhibitor of a Wnt/β-catenin pathway is an antibody, or an antigen-binding fragment thereof, the antibody is a humanized antibody. In an embodiment wherein the inhibitor of a Wnt/β-catenin pathway is an antibody, or an antigen-binding fragment thereof, the antibody is a human antibody. The term "human antibody", as used herein, is intended to include antibodies having variable regions in which both the framework and CDR regions are sequences of human origin or identical thereto other than antibodies naturally occurring in a human or made in a human. Furthermore, if the antibody (e.g. an intact antibody rather than, for example, an Fab fragment) contains a constant region, the constant region also is derived from such human sequences, e.g., human germline sequences, or mutated versions of human germline sequences. The human antibodies of the invention may include amino acid residues not encoded by human sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences. In one non-limiting embodiment, where the human antibodies are human monoclonal antibodies, such antibodies can be produced by a hybridoma which includes a B cell obtained from a transgenic nonhuman animal, e.g., a transgenic mouse, having a genome comprising a human heavy chain transgene and a light chain transgene fused to an immortalized cell. In an embodiment, the antigen-binding fragment is a Fab, F(ab)2, or a single-chain Fv (scFv), which is less than the whole antibody but which is an antigen-binding portion and which competes with the intact antibody of which it is a fragment for specific binding. In an embodiment, the antibody is a monoclonal antibody.

Examples of small molecules inhibitors of the Wnt/beta-Catenin pathway include:

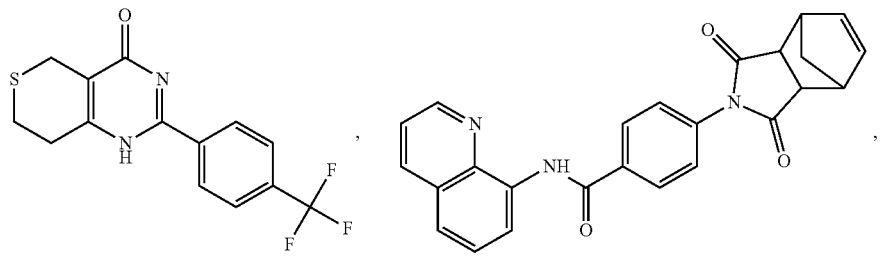

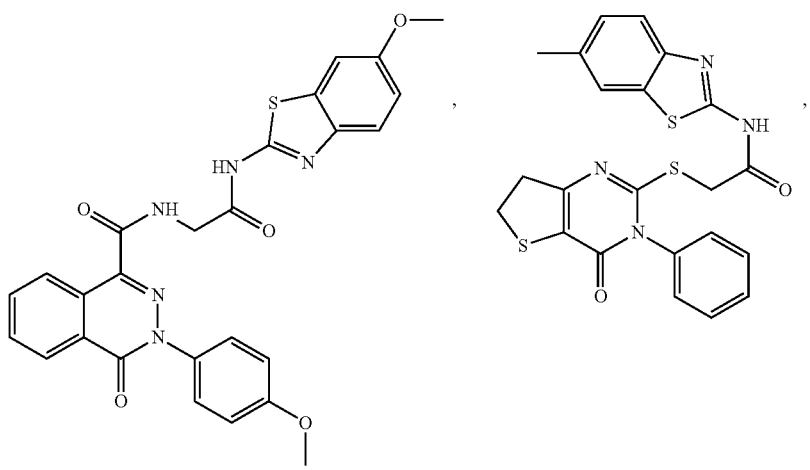

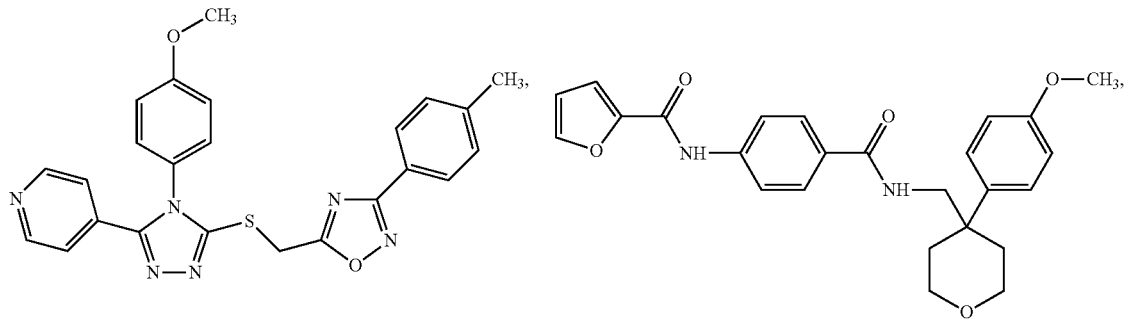

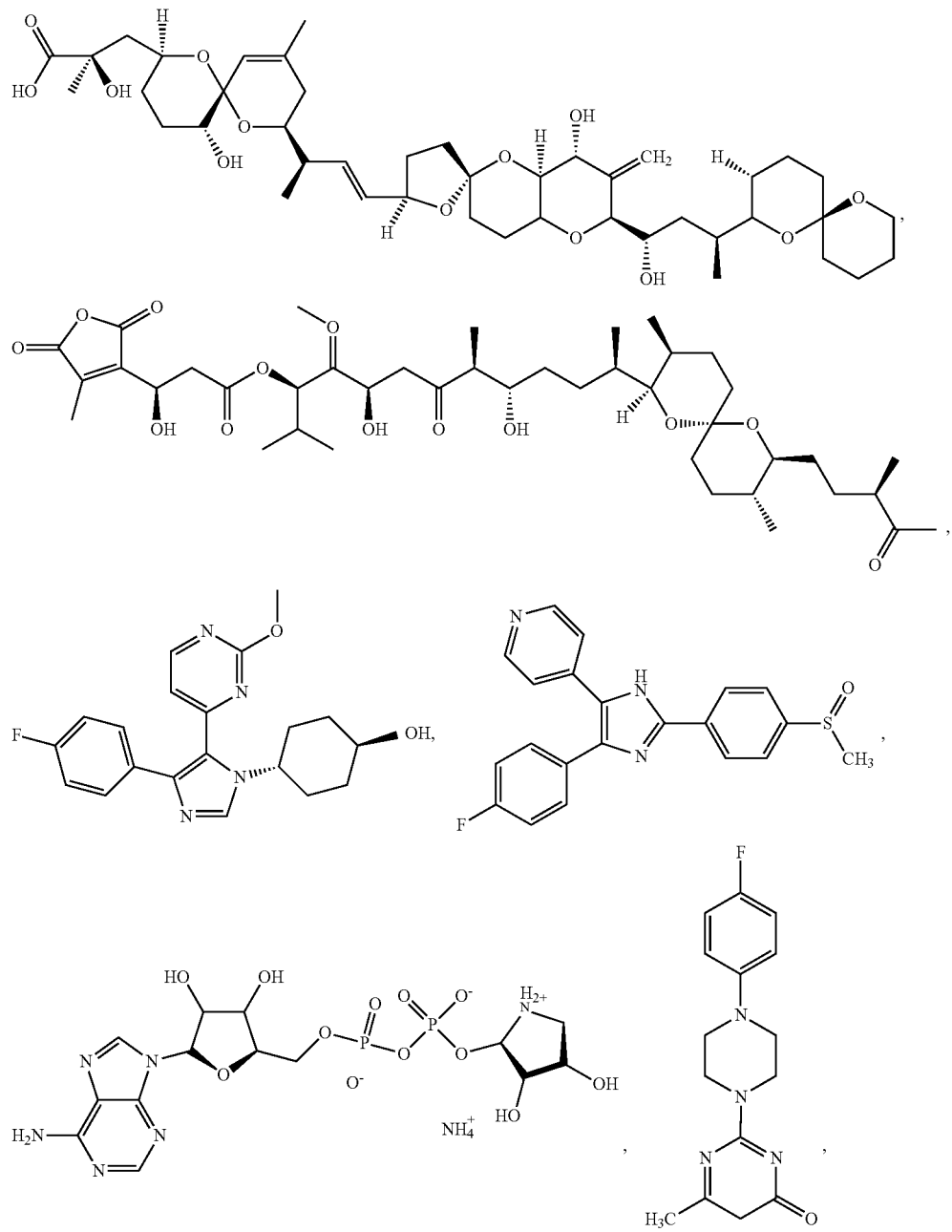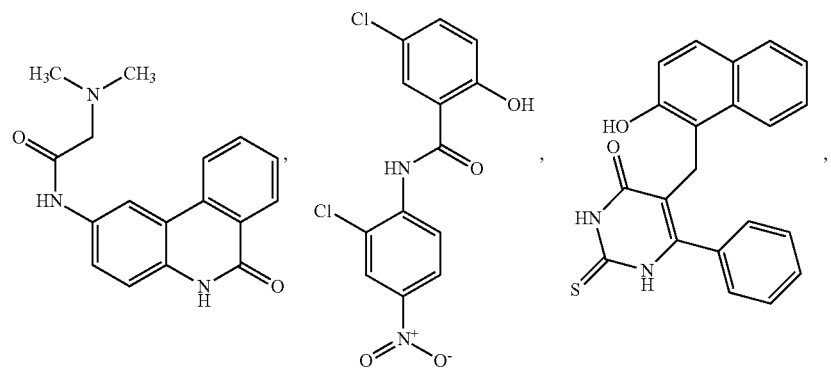

-continued
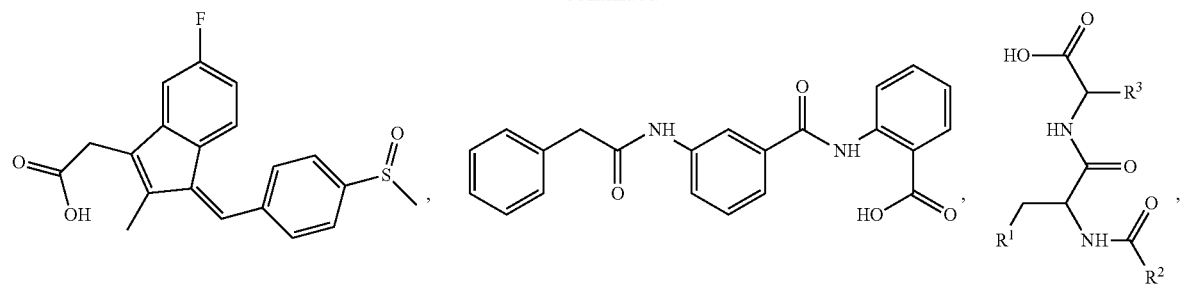
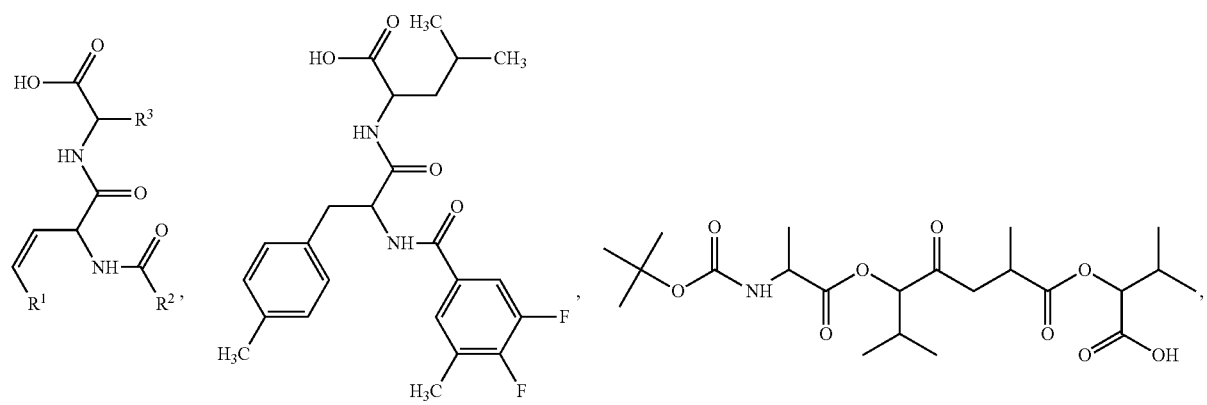
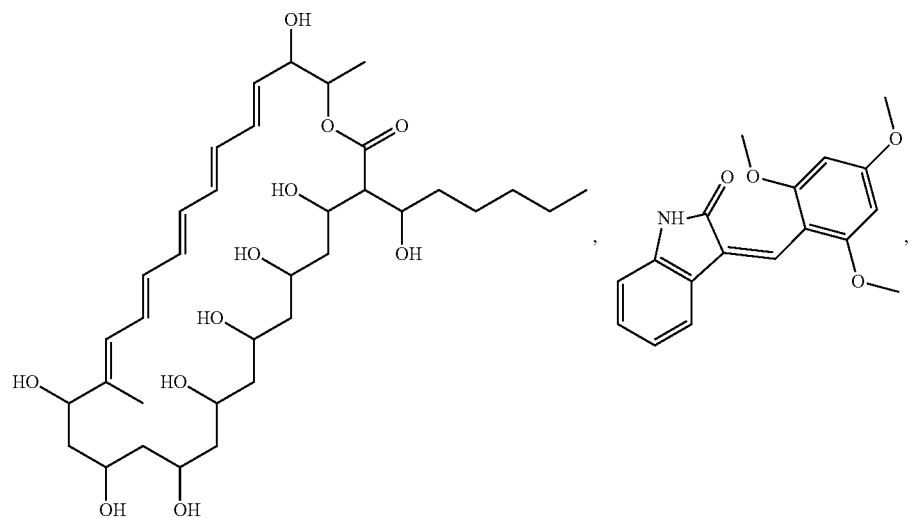
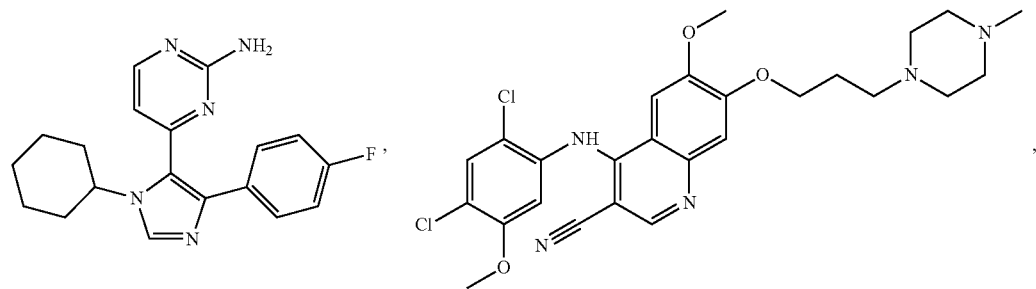

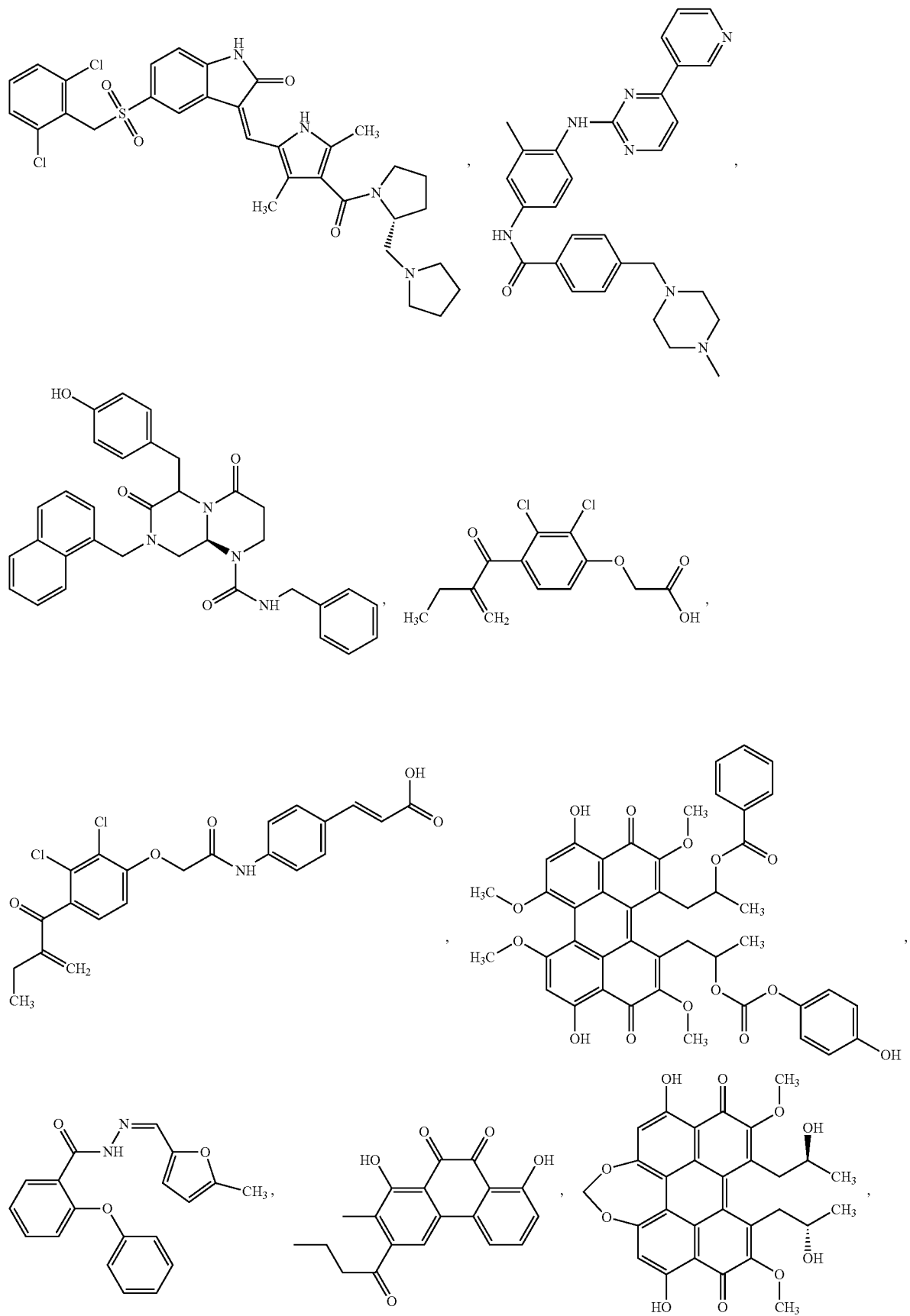

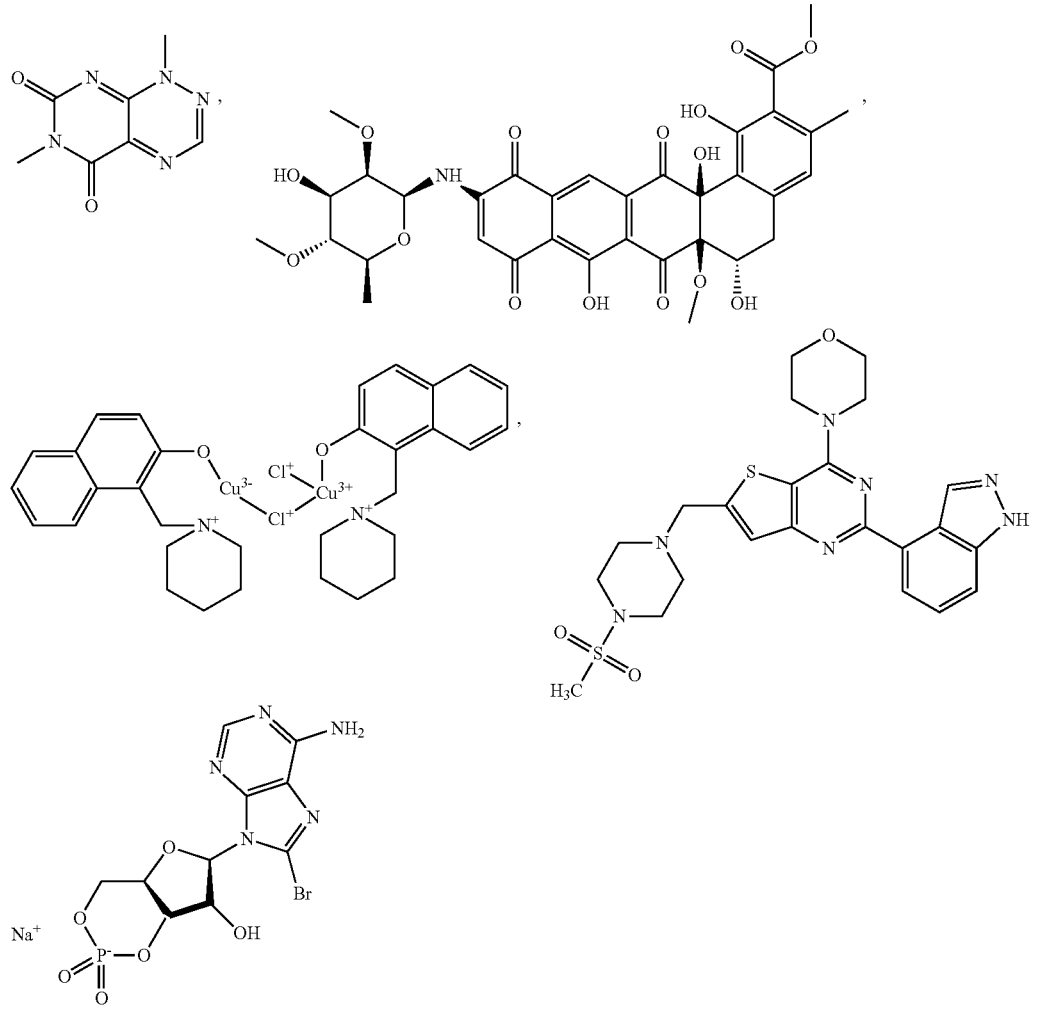

or salts or conjugates thereof (see Voronkov and Krauss, *Curr Pharm Des.* 2012 February; 19(4): 634-664).

In an embodiment an amount of 1-500 μg Wnt/β-catenin pathway inhibitor/cm stent area is an exemplary dose for the drug eluting stent embodiment. In a non-limiting embodiment, the drug eluting stent in accordance with the present invention, has a maximum diameter when expanded of (i) 1.0 mm to about 20 mm, (ii) 3 0 mm to about 15 mm, or (iii) 4 mm to about 12 mm. In a non-limiting embodiment, the drug eluting stent in accordance with the present invention, has a minimum inner diameter when in a deployable phase of 0 μm (i.e., touching) to about 1000 μm, more preferably from about 0 μm to about 500 μm, and most preferably from about 0 μm to about 200 μm.

Non-limiting embodiment examples of polymer coatings are (i) at a thickness of 2 μm to 50 μm, (ii) from 4 μm to 25 μm, (iii) from 5 μm to 20 μm, or (iv) from 13 to about 15 μm.

In one embodiment, the polymer coated stent can comprise a second coating layer which, optionally, can control the release of the drug in a manner that prolongs the release profile.

In one embodiment, the coating/drug combination is configured to provide an extended elution profile that can elute substantially constant levels of drug over (i) 3 months, (ii) 6 months, (iii) 9 months, or (iv) 12 months, or (v) more than 12 months In one embodiment, the compositions of the invention comprise an additional drug in addition to the Wnt/β-catenin pathway inhibitor.

In one embodiment, the compositions of the invention comprising a polymer-coated stent can comprise one or more different additional polymer(s). In one embodiment, the compositions of the invention comprising a polymer-coated stent comprise a co-polymer.

Non-limiting exmaples of stent lengths are 2.5 mmm to 35mm. The average stent diameter was shorter for DES (2.89 mm) versus BMS (3.00 mm)

The phrase "and/or" as used herein, with option A and/or option B for example, encompasses the individual embodiments of (i) option A alone, (ii) option B alone, and (iii) option A plus option B.

It is understood that wherever embodiments are described herein with the language "comprising," otherwise analogous embodiments described in terms of "consisting of" and/or "consisting essentially of" are also provided.

As used herein, "surgery," and all grammatical forms thereof, shall mean any action involving cutting of a tissue, resection of a tissue or organ or vessel, or penetration of skin, of a human subject for the purposes of medical treatment (including, e.g., penetration of skin for placing a stent into a distant blood vessel site for subsequent moving to a predetermined site in a blood vessel).

Where aspects or embodiments of the invention are described in terms of a Markush group or other grouping of alternatives, the present invention encompasses not only the entire group listed as a whole, but each member of the group subjectly and all possible subgroups of the main group, but also the main group absent one or more of the group members. The present invention also envisages the explicit exclusion of one or more of any of the Markush group members in the claimed invention.

All combinations of the various elements described herein are within the scope of the invention unless otherwise indicated herein or otherwise clearly contradicted by context.

In the event that one or more of the literature and similar materials incorporated by reference herein differs from or contradicts this application, including but not limited to defined terms, term usage, described techniques, or the like, this application controls.

This invention will be better understood from the Experimental Details, which follow. However, one skilled in the art will readily appreciate that the specific methods and results discussed are merely illustrative of the invention as described more fully in the claims that follow thereafter.

EXPERIMENTAL DETAILS

Introduction

The Wnt/beta-catenin signaling pathway belongs to a small group of highly conserved signaling networks that support normal development and adult tissue homeostasis. Beta-catenin, the central downstream effector of this signaling pathway, also plays a structural role in cell and tissue integrity as part of the cadherin-mediated cell-cell adhesion complex. From the perspective of vascular biology, the importance of this pathway in endothelial cells (ECs), but not vascular smooth muscle cells (SMCs), has been tested and described in the literature. EC-specific genetic inactivation of beta-catenin in the mouse shows an overtly normal vascular pattern in non-neural tissues, including the liver, lung, skin, jaw, and tail, but major defects in the vasculature of the central nervous system (CNS). Mild patterning defects restricted to the large vessels of the vitelline and umbilical cord have been also described. Therefore, in the vascular system of the embryo proper, beta-catenin signaling seems to be required only in the ECs of the CNS circulation; loss of beta-catenin in ECs of other vascular beds does not appear to have significant effects on blood vessel structure and function.

Results

Figures 5A, 5B, 5C, 5D, 5E, 5F:
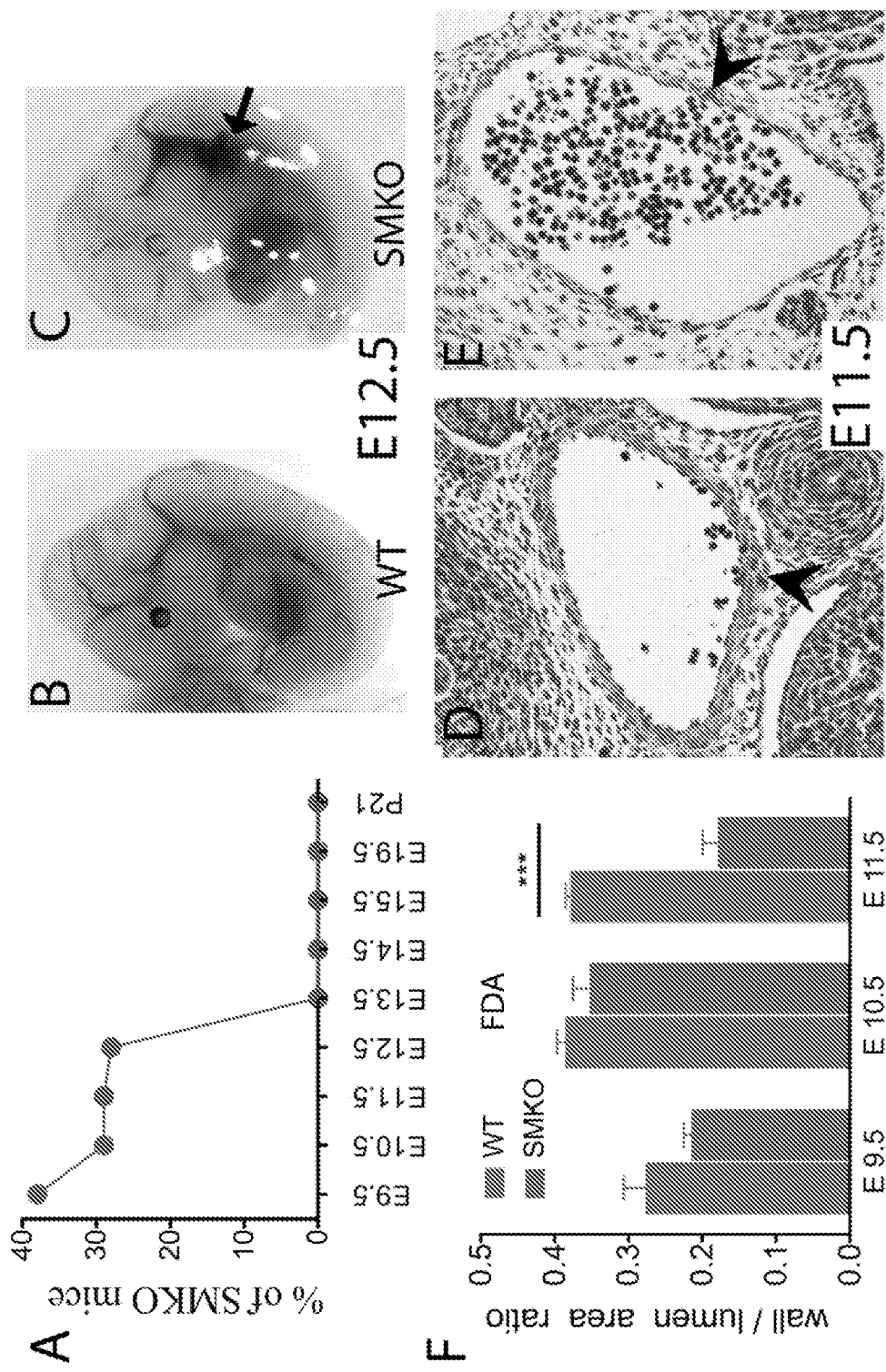
FIG. 5. Smooth muscle inactivation of beta-catenin caused embryonic lethality by E13.5 and was associated with abnormal arterial systemic circulation. A) No beta-catenin smooth muscle knockout (SMKO) embryo was found at E13.5 or further (93 embryos and 215 pups were analyzed). B) Wild type (WT) embryo at E12.5. C) SMKO embryo at E12.5 showing enlarged blood vessels (arrow). D) Fused dorsal aorta of a WT embryo showing a normal vessel wall (arrowhead). E) Fused dorsal aorta in a SMKO embryo showing an enlarge diameter and thinner vessel wall (arrowhead). F) Significant reduction in wall thickness of the fused dorsal aorta was found by E11.5 in the SMKO compared to WT; ***=p<0.001.
Figures 6A, 6B, 6C, 6D, 6E, 6F:
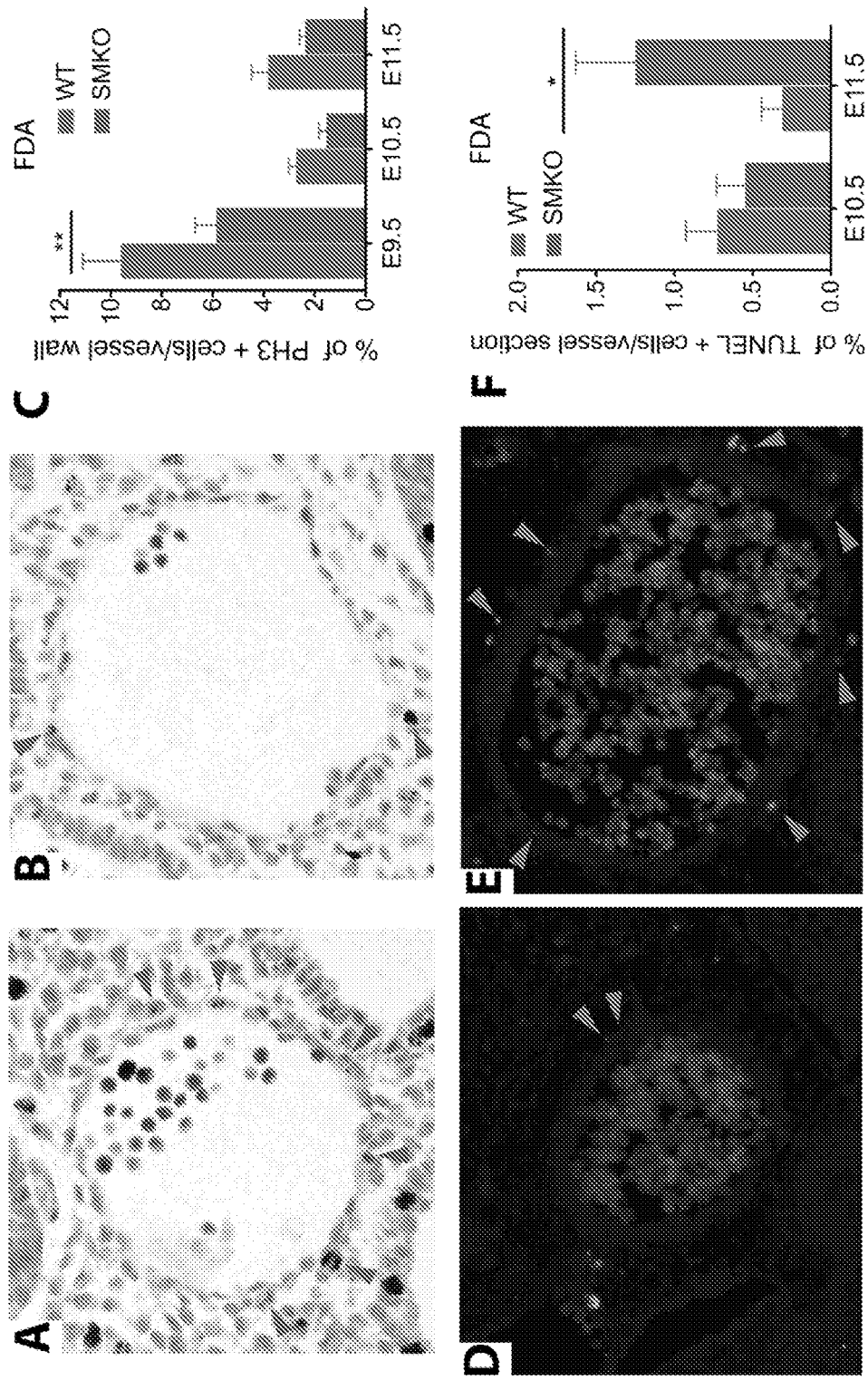
FIG. 6. Vascular smooth muscle cell beta-catenin promoted proliferation and survival in the arterial vessel wall during development. A) Fused dorsal aorta at E9.5 in control embryos showed several proliferative cells (arrowheads) identified by immunohistochemistry for phospho-histone 3. B) Fused dorsal aorta at E9.5 in SMKO embryos showed reduced number of proliferative cells (arrowheads). C) Significant reduction in the percentage of proliferative cells in the vessel wall of SMKO embryos compared to controls; **=p<0.01. D) Fused dorsal aorta at E11.5 in control embryos (WT) showing few apoptotic cells (arrowheads) in the vessel wall identified by TUNEL assay. E) Fused dorsal aorta at E11.5 in SMKO embryos showing abundant apoptotic cells in the vessel wall (arrowheads). F) Significant increase in the percentage of apoptotic cells in the vessel wall of SMKO embryos compared to WT; *=p<0.05.
Figure 7:
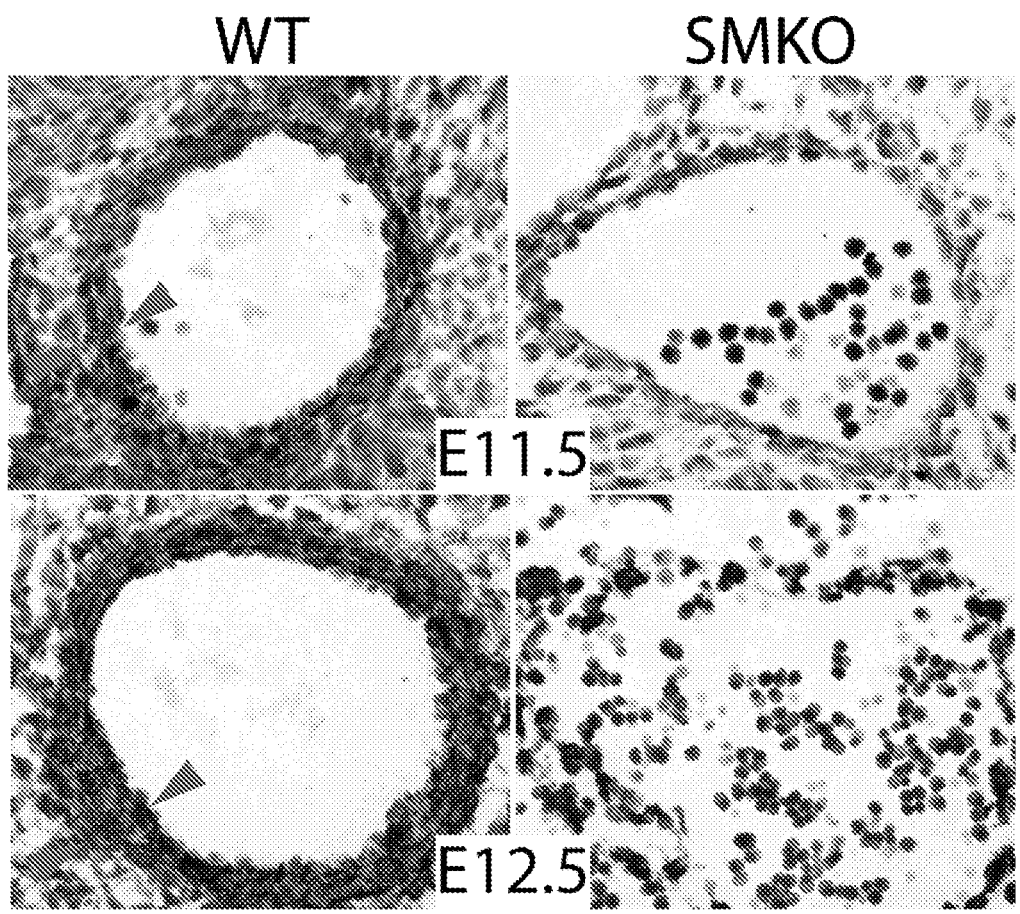
FIG. 7. Vascular smooth muscle cell beta-catenin was essential for smooth muscle investment of arterial vessels during development. Smooth muscle cells (SMCs) were identified by immunohistochemistry for SM22 alpha (brown color). In the control embryos (WT), SMCs were recruited and formed an organized multilayered vessel wall (between arrowheads), this process failed to happen when beta-catenin was absent in SMCs (SMKO) resulting in dilated vessels that lacked a SMC layer (right panels).
Figures 8A, 8B, 8C:
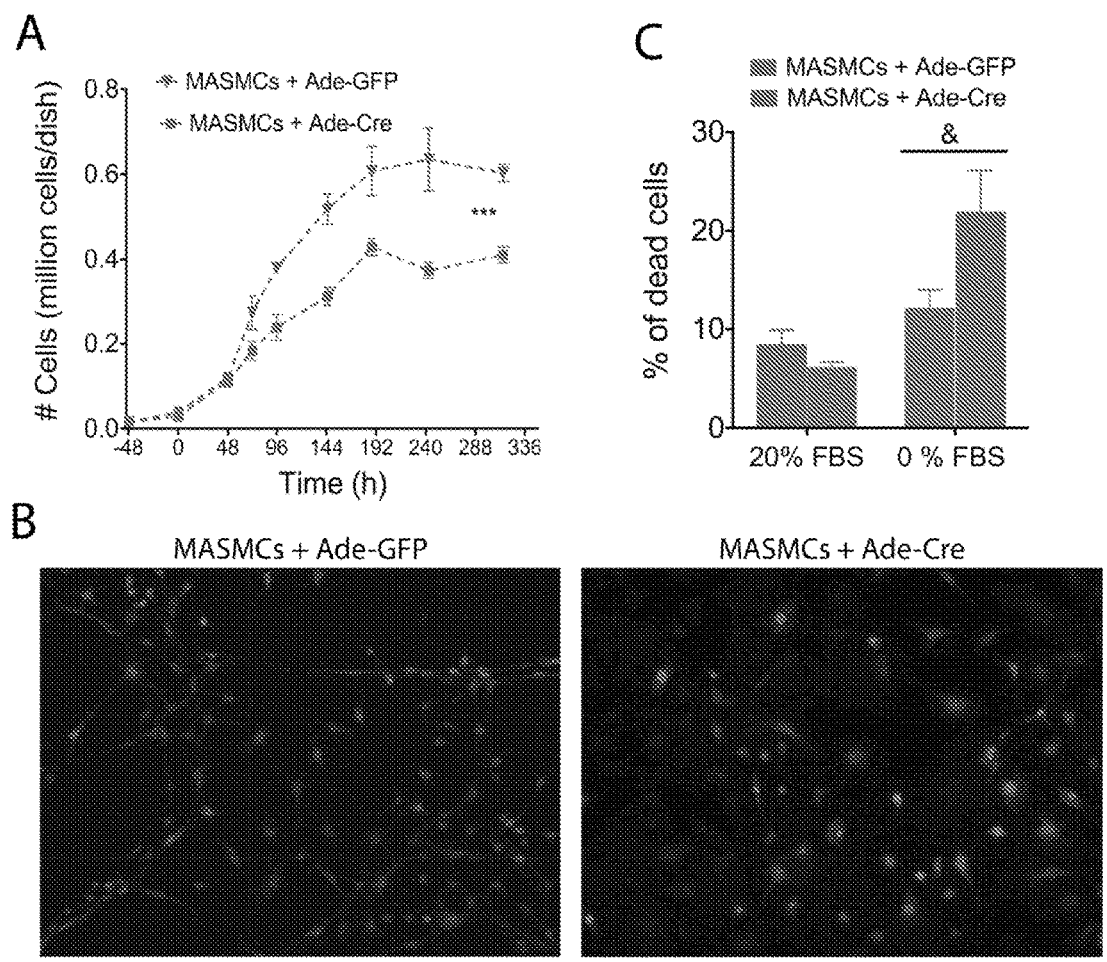
FIG. 8. In primary vascular smooth muscle cells beta-catenin was necessary for cell population growth and survival. A) Vascular SMCs lacking beta-catenin (MASMCs+Ade-Cre) showed significant slower rate of growth and lower plateau when cultured in standard conditions compared to control cells (MASMCs+Ade-GFP); ***=p<0.001. B) Vascular smooth muscle cells died more under serum starvation compared to control cells; dead cells in red and live cells in green were identified by a LIVE/DEAD assay. C) Significant increase in cell death in cells lacking beta-catenin compared to control cells under serum starvation (0% FBS); &=p<0.05.
Figure 9:
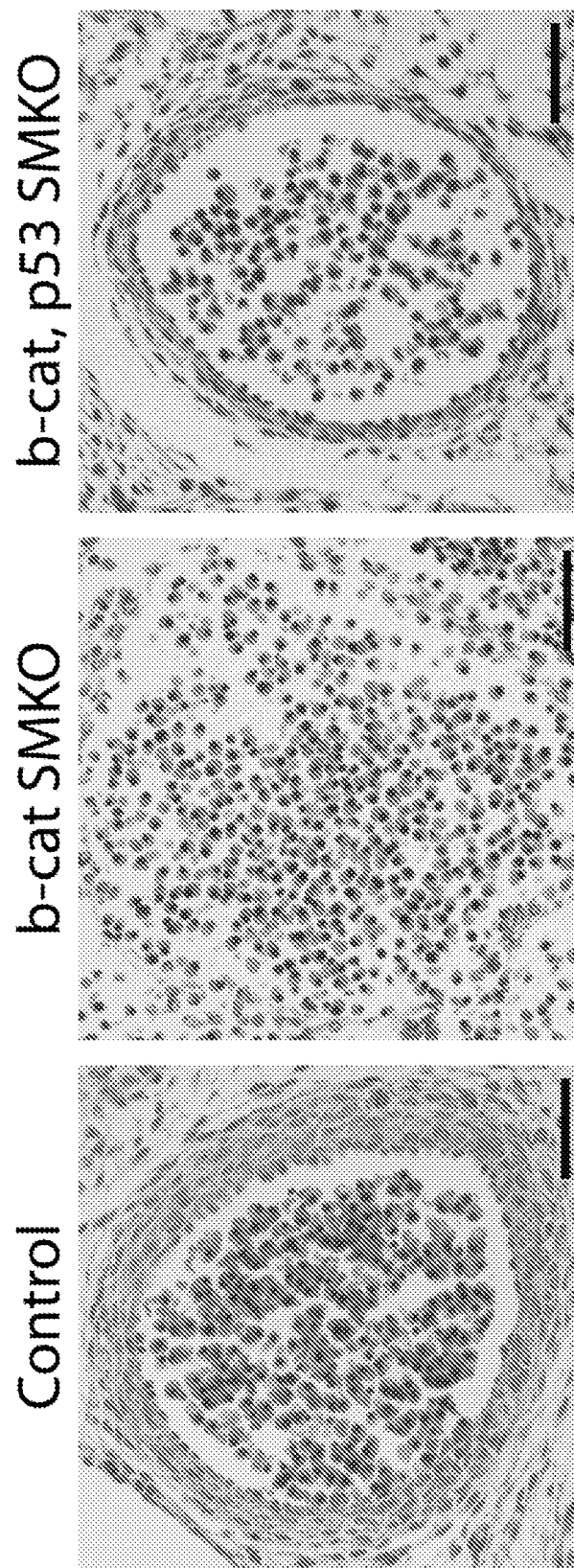
FIG. 9. The loss-of-function of p53 in vascular smooth muscle cells suppressed the effect of the loss-of-function of beta-catenin (b-cat). The left panel shows a normal aorta at E12.5; the middle panel shows that the inactivation of beta-catenin in smooth muscle cells (b-cat SMKO) compromised the formation of a competent vessel wall; the right panel shows a significant partial recovery of vessel wall formation when both p53 and beta-catenin are inactivated in SMCs (b-cat, p53 SMKO). This indicates that beta-catenin is essential for SMC investment of arterial vessels and this function is carried out in part by inhibiting p53 in vascular SMCs during development.
Figure 10:
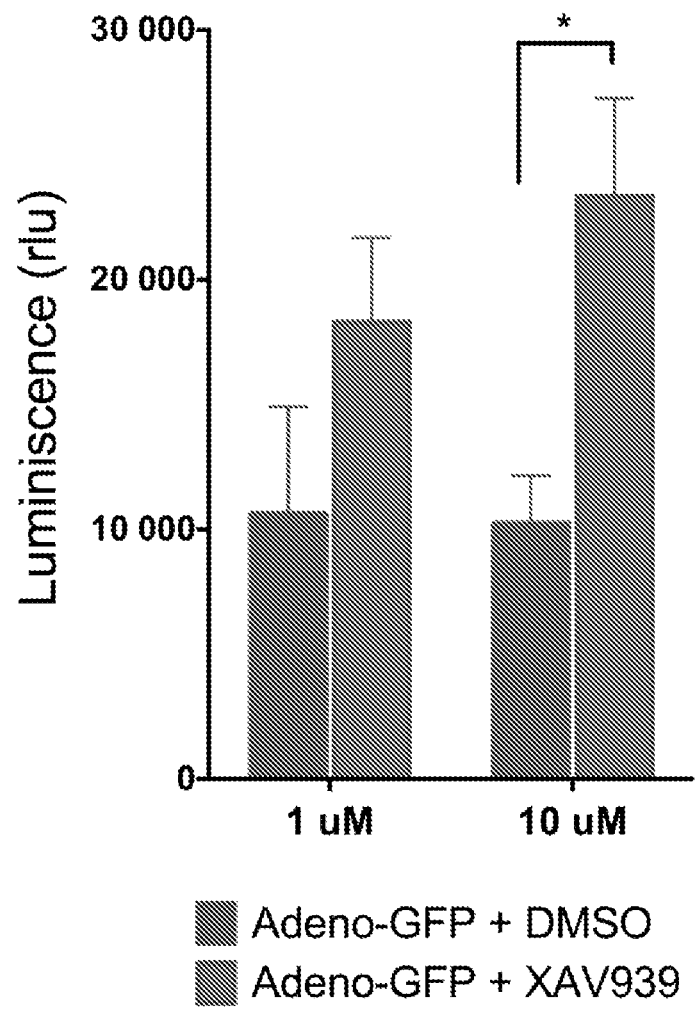
FIG. 10. XAV939, an inhibitor of beta-catenin signaling, induced p53 activity in control primary vascular SMCs (Adeno-GFP) in a dose dependent manner. The activity of p53 was measured by a luciferase-based reporter assay. A significant increase in p53 activity is induced by 10 uM XAV939 compared to vehicle (DMSO). *=p<0.05.
Figure 11:
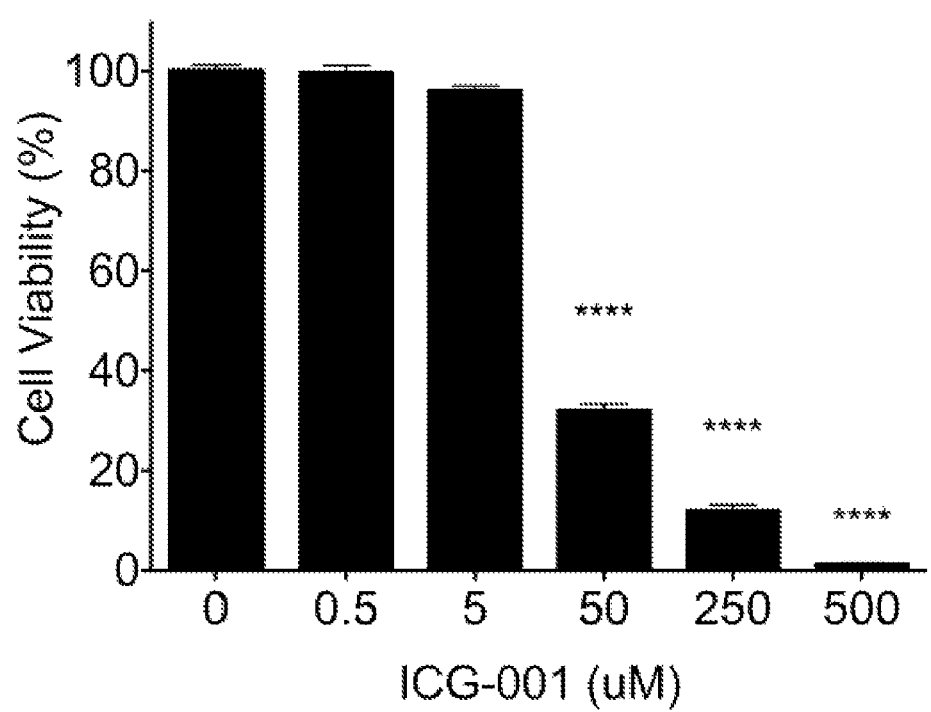
FIG. 11. Primary WT mouse aortic smooth muscle cells cultured in 10% FBS/DMEM medium were exposed to increasing concentrations of ICG-001 or vehicle (triplicates for each concentration). Cell viability was measured 48 hours after treatment by alamarBlue Assay. Cell viability (%, relative to vehicle treated cells, which were set as 100%) is plotted against the concentration of ICG-001 (uM). ICG-001 significantly decreases viability of MASMCs in culture in a dose-response manner. ***=p<0.0001 when compared to vehicle (0 uM).

In order to test the role of Wnt/beta-catenin signaling in vascular SMC biology, beta-catenin was specifically inactivated in SMCs, using a genetic approach in the mouse. Absence of beta-catenin in SMCs resulted in an abnormal systemic circulation unable to support embryonic development (FIG. 5). Arterial blood vessels showed larger diameters and thinner walls, decreased proliferation and increased apoptosis (FIGS. 5 and 6). After midgestation, dilated arterial vessels without an evident SMC layer were observed (FIG. 7). It was determined that genetic inhibition of beta-catenin in primary vascular SMCs in culture also resulted in decreased growth and increased cell death (FIG. 8). It was determined that increased p53 activity in SMCs partially explains the effects of inactivating beta-catenin (FIG. 9). Interestingly, inhibitors of beta-catenin that reduce the overall cellular levels of beta-catenin (e.g., XAV939) also induced p53 activity in wild type vascular SMCs (FIG. 10). When beta-catenin was inactivated in SMCs in adulthood using a temporally regulated genetic system, it was found that beta-catenin inactivation caused a significant change in the response to vascular injury—after carotid artery ligation, mice lacking beta-catenin in SMCs showed a significant reduction in neointima formation (stenosis) compared to control mice, which was associated with decreased proliferation and increased apoptosis (FIG. 1). Finally, the effect of a beta-catenin inhibitor on vascular smooth muscle cell viability is shown in FIG. 11. It can be seen that ICG-001 significantly decreases viability of MASMCs in culture in a dose-response manner compared to control.

Altogether, these studies indicate that inhibiting beta-catenin in SMCs decreases cell proliferation, increases apoptosis, prevents vascular SMC investment of arterial vessels during development, and reduces neointima formation (stenosis) after vascular injury in adulthood. Inhibiting Wnt/beta-catenin signaling in the vascular system, outside of the CNS circulation, does not affect EC function but significantly inhibits SMC function. This cell type specificity makes inhibition of Wnt/beta-catenin signaling an ideal strategy for the treatment or prevention of restenosis after angioplasty and stent placement.

This invention addresses the critical limitations of existing DESs by releasing an inhibitor of Wnt/beta-catenin signaling rather than current broadly active anti-proliferative agents such as paclitaxel or sirolimus. The laboratory findings here indicate that a Wnt/beta-catenin inhibitor limits vascular SMC proliferation and survival, and thus opposes restenosis. At the same time inhibition of Wnt/beta-catenin signaling will not affect most EC functions, allowing endothelialization of stent struts and inhibition of clot formation and inflammation, which in turn will reduce the risk of in-stent thrombosis. Therefore, this invention can avoid, if desired, long-term dual antiplatelet therapy. This reduces the risk of bleeding and health care costs. It is also suitable to use in patients for whom existing DESs are not indicated.

Figure 4:
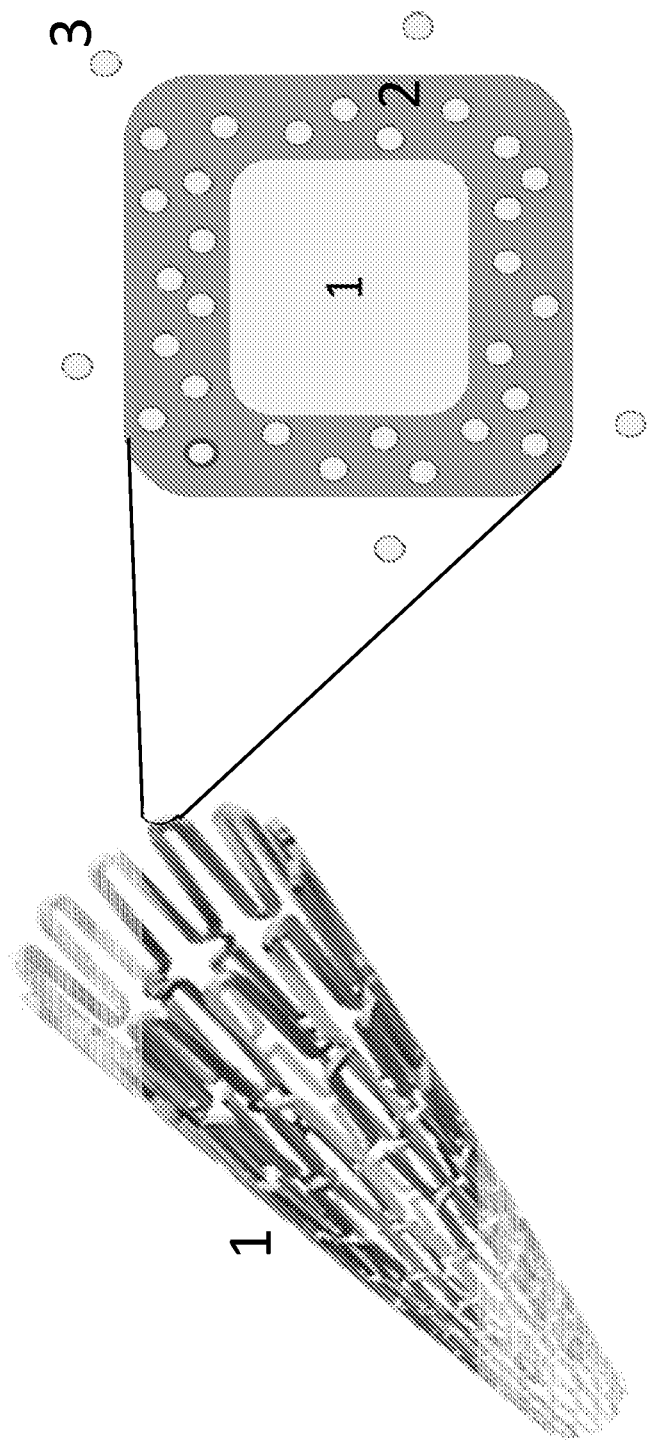
FIG. 4: Components of example stent: 1) stent platform or scaffold, 2) a polymeric coating (in blue), and 3) a pharmacologic or biologic inhibitor of Wnt/beta-catenin signaling (in yellow). The inhibitor is mixed within the polymeric coating and is released over a sustained period of time. Modified from the world wide web as andramed.com/index.php?open=products&id=7.

Generally the present invention can include a stent platform or scaffold, a polymeric coating, and a pharmacologic or biologic inhibitor of Wnt/beta-catenin signaling (FIG. 4). The inhibitor can be mixed within the polymeric coating, for example, and is released over a sustained period of time (for example, weeks to months). Inhibitors of the Wnt/beta-catenin signaling have been developed and are known in the art. The status of several such inhibitors as of late 2010 is summarized in Table 1.

TABLE I

Status of Wnt Pathway Drug Discovery

| | Company/Institution | Drug type | Target | Stage |
|---|---|---|---|---|
| Wnt/receptor interactions | Genentech | Soluble Receptor Biologic | Wnt ligands | Discovery |
| | UCSF | Antibody | Wnt1, Wnt2 | Discovery |
| | Oncomed | Antibody | Fzds | Phase I 2011 |
| Cytosolic signaling | St. Jude Children's | Small Molecule | Dvl | Discovery |
| | Novartis | Small Molecule | Tankyrase 1, 2 | Discovery |
| | UTSW | Small Molecule | Axin | Discovery |
| | UTSW | Small Molecule | Porcupine | Discovery |
| | Theriac Pharmaceutical | Small Molecule | β-catenin | Phase I 2010 |
| | Fate Therapeutics | Small Molecule | Unknown | Phase I |

TABLE I-continued

Status of Wnt Pathway Drug Discovery

| | Company/ Institution | Drug type | Target | Stage |
|---|---|---|---|---|
| Nuclear signaling | Harvard/ Novartis | Small Molecule | TCF/β-catenin | Discovery |
| | USC | Small Molecule | CBP | Discovery |

(See Joshua C. Curtin and Matthew V. Lorenzi, Drug Discovery Approaches to Target Wnt Signaling in Cancer Stem Cells. Oncotarget 2010; 1: 563-566).

As shown, the Wnt/b-catenin pathway has been targeted at multiple levels. By targeting upstream Wnt activation, or supporting destruction complex function, most of these strategies seek to limit the amount of beta-catenin that accumulates in the nucleus. The two nuclear strategies use small molecules intended to block interaction of beta-catenin with either DNA-binding TCF proteins or the CBP co-activator. Typically, stents are manufactured from biologically inert metals such as stainless steel. In recent years, however, metallic alloys such as cobalt—chromium or platinum—chrome have superseded steel as the material of choice for stent design. These metallic alloys have been developed to achieve increased levels of strength and lower X-ray attenuation compared to stainless steel, allowing newer stents to be designed with significantly thinner struts that do not impair the resulting strength, corrosion resistance, or radio-opacity of the device. Further development in stent design is currently centered on the assessment of stronger metallic alloys, compound metals, and bioabsorbable materials. Polymer coatings that are applied to the stent surface serve as drug carriers and permit controlled drug release. The most successful method of facilitating drug adhesion and delivery from a stent has involved the use of permanent synthetic polymer coating materials such as polyethylene-co-vinyl acetate (PEVA), poly-n-butyl methacrylate (PBMA), and the tri-block co-polymer poly(styrene-b-isobutylene-b-styrene) (SIBS). In recent years these permanent polymers have been superseded by advanced biocompatible permanent polymers such as phosphorylcholine (PC) and the co-polymer poly(vinylidene fluoride-co-hexafluoropropylene) (PVDF-HFP). By carefully mixing anti-restenotic drugs with these materials, a drug-polymer matrix may be formed and applied to the surface of the stent platform. Upon deployment, drug-delivery is driven by diffusion from the matrix and the rate of this diffusion is dictated by the type, composition and number of polymers used in the drug-polymer matrix. Other platforms for drug-eluting stents feature polymers that biodegrade after drug elution, resulting in a stent surface similar to that of a bare-metal stent, and fully bioresorbable drug-eluting vascular scaffolds.

REFERENCES

1. Voronkov and Krauss, *Curr Pharm Des*. 2012 February; 19(4): 634-664.

What is claimed is:

1. A product comprising a stent for a human blood vessel which comprises (i) a scaffold coated with a polymer, which polymer is impregnated with, adsorbed with, or coated with an inhibitor of a Wnt/β-catenin pathway, or (ii) a scaffold which is impregnated with, adsorbed with, or coated with, an inhibitor of a Wnt/β-catenin pathway, wherein the inhibitor comprises

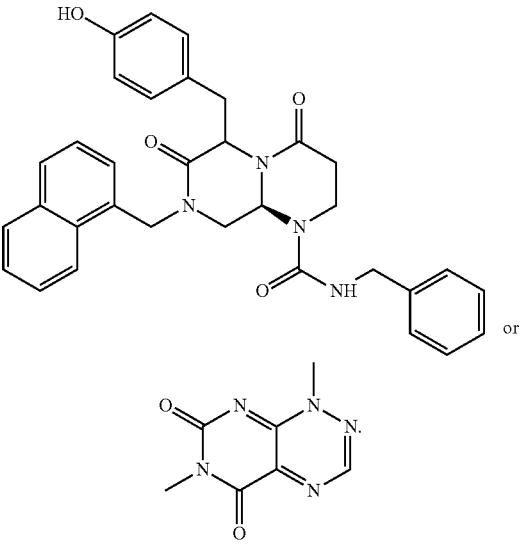

or

2. The product of claim 1, wherein the stent is a shaped to be suitable as an endovascular stent.

3. The product of claim 1, wherein at least 50% of the inhibitor of a Wnt/β-catenin pathway elutes from the stent.

4. The product of claim 1, wherein at least 90% of the inhibitor of a Wnt/β-catenin pathway elutes from the stent over a time period of 1 to 150 days.

5. The product of claim 1, wherein the stent comprises a scaffold impregnated with, adsorbed with, or coated with, an inhibitor of a Wnt/β-catenin pathway.

6. The product of claim 1, wherein the stent comprises a scaffold coated with a polymer impregnated with, adsorbed with, or coated with an inhibitor of a Wnt/β-catenin pathway.

7. The product of claim 6, wherein the inhibitor of a Wnt/β-catenin pathway is adsorbed within the polymer and/or adsorbed to a surface of the polymer.

8. The product of claim 6, wherein the inhibitor of a Wnt/β-catenin pathway is coated on the polymer.

9. The product of claim 6, wherein the polymer is not prothrombotic.

10. The product of claim 6, wherein the polymer comprises one or more of poly(n-butyl methacrylate), poly(ethylene-co-vinyl acetate), poly(styrene-b-isobutylene-b-styrene) or poly(vinylidene fluoride-co-hexafluoropropylene).

11. The product of claim 6, wherein the polymer comprises phosphorylcholine.

12. The product of claim 1, wherein the polymer is biodegradable.

13. The product of claim 1, wherein the stent is bioresorbable.

14. A method for performing an angioplasty in a mammalian subject comprising surgically inserting the stent of claim 1 into the a vascular vessel and expanding the stent therein so as perform the angioplasty.

15. A method for reducing restenosis in a vascular vessel at risk for restenosis of a mammalian subject, comprising surgically inserting the stent of claim 1 into the lumen of the vascular vessel at the site deemed at risk of restenosis, so as to reduce the risk of restenosis.

16. The method of claim 14, wherein the vascular vessel is not a CNS vascular vessel.

17. The method of claim 14, wherein the vascular vessel is a coronary vascular vessel.

18. The method of claim 14, wherein the subject has atherosclerotic disease of the vascular vessel.

19. The method of claim 14, wherein the subject has undergone an angioplasty of the vascular vessel.

* * * * *